(12) United States Patent
Ethridge et al.

(10) Patent No.: US 10,948,130 B2
(45) Date of Patent: Mar. 16, 2021

(54) REAL TIME INTEGRITY MONITORING OF ON-SHORE PIPES

(71) Applicant: FLEXSTEEL PIPELINE TECHNOLOGIES, INC., Houston, TX (US)

(72) Inventors: Andrew David Ethridge, Houston, TX (US); Alexander Lee Winn, Houston, TX (US)

(73) Assignee: Trinity Bay Equipment Holdings, LLC, Houston, TX (US)

(*) Notice: Subject to any disclaimer, the term of this patent is extended or adjusted under 35 U.S.C. 154(b) by 215 days.

(21) Appl. No.: 15/773,109

(22) PCT Filed: Nov. 2, 2015

(86) PCT No.: PCT/US2015/058618
§ 371 (c)(1),
(2) Date: Jul. 30, 2018

(87) PCT Pub. No.: WO2017/078670
PCT Pub. Date: May 11, 2017

(65) Prior Publication Data
US 2018/0320826 A1 Nov. 8, 2018

(51) Int. Cl.
*G01N 25/12* (2006.01)
*F17D 5/02* (2006.01)
(Continued)

(52) U.S. Cl.
CPC .................. *F17D 5/02* (2013.01); *F17D 1/04* (2013.01); *F17D 1/05* (2013.01); *F17D 1/08* (2013.01);
(Continued)

(58) Field of Classification Search
CPC ..... F17D 5/02; F17D 1/02; F17D 1/04; F17D 1/05; F17D 1/08; F17D 1/18; G01M 3/002; G01N 27/20
(Continued)

(56) References Cited

U.S. PATENT DOCUMENTS

| 4,450,711 A | 5/1984 | Claude |
| 6,171,025 B1 | 1/2001 | Langner et al. |

(Continued)

FOREIGN PATENT DOCUMENTS

| AU | 2015413844 | 9/2019 |
| CA | 2929373 | 5/2015 |

(Continued)

OTHER PUBLICATIONS

Patent Office of the Cooperation Council for the Arab States of the Gulf; Examination Report, issued in connection to Application No. GC2015-30311; dated Oct. 30, 2019; 5 pages; GCC.

(Continued)

*Primary Examiner* — Tarun Sinha
(74) *Attorney, Agent, or Firm* — Greenberg Traurig, LLP; Dwayne Mason; Ira Hatton

(57) ABSTRACT

A method includes providing a length of pipeline that has a housing defining a central bore extending the length of the pipe and a space formed within the housing and extending the length of the pipe. At least one condition within the space is continuously monitored within the space to detect in real time if a change in the housing occurs.

20 Claims, 3 Drawing Sheets

(51) Int. Cl.

| | | |
|---|---|---|
| *F17D 1/04* | (2006.01) | |
| *F17D 1/08* | (2006.01) | |
| *F17D 5/06* | (2006.01) | |
| *F17D 3/01* | (2006.01) | |
| *F17D 1/18* | (2006.01) | |
| *F17D 5/04* | (2006.01) | |
| *F17D 1/05* | (2006.01) | |
| *F17D 5/00* | (2006.01) | |
| *G01M 3/00* | (2006.01) | |
| *G01M 3/18* | (2006.01) | |
| *G01M 3/28* | (2006.01) | |
| *G01N 27/20* | (2006.01) | |
| *G01N 33/22* | (2006.01) | |
| *G01N 33/28* | (2006.01) | |

(52) U.S. Cl.
CPC .............. *F17D 1/18* (2013.01); *F17D 3/01* (2013.01); *F17D 5/005* (2013.01); *F17D 5/04* (2013.01); *F17D 5/06* (2013.01); *G01M 3/002* (2013.01); *G01M 3/18* (2013.01); *G01M 3/2815* (2013.01); *G01N 25/12* (2013.01); *G01N 27/20* (2013.01); *G01N 33/225* (2013.01); *G01N 33/2811* (2013.01)

(58) Field of Classification Search
USPC ............................................. 73/23.2
See application file for complete search history.

(56) References Cited

U.S. PATENT DOCUMENTS

| | | | |
|---|---|---|---|
| 6,634,388 | B1 | 10/2003 | Taylor et al. |
| 7,688,071 | B2 | 3/2010 | Cheng et al. |
| 7,768,270 | B2 | 8/2010 | Brusco et al. |
| 8,030,946 | B2 | 10/2011 | Brusco et al. |
| 8,893,748 | B2 | 11/2014 | Malas et al. |
| 10,677,394 | B2 | 6/2020 | Ethridge et al. |
| 2005/0155663 | A1 | 7/2005 | Dhellemmes |
| 2008/0048682 | A1 | 2/2008 | Brusco et al. |
| 2009/0066330 | A1 | 3/2009 | Cheng et al. |
| 2010/0277188 | A1 | 11/2010 | Brusco et al. |
| 2011/0153225 | A1* | 6/2011 | Mangal ............... G01F 1/00 702/24 |
| 2011/0154884 | A1 | 6/2011 | Weppenaar |
| 2013/0014833 | A1 | 1/2013 | Geertsen |
| 2013/0154666 | A1 | 6/2013 | Albaladejo et al. |
| 2013/0340793 | A1 | 12/2013 | Lund |
| 2014/0124077 | A1* | 5/2014 | Malas ............... F16L 9/19 138/114 |
| 2014/0241810 | A1 | 8/2014 | Lynch et al. |
| 2018/0274731 | A1 | 9/2018 | Ethridge |

FOREIGN PATENT DOCUMENTS

| | | | |
|---|---|---|---|
| CN | 101016975 | | 8/2007 |
| CN | 204533856 U | * | 8/2015 |
| CN | 108474521 | | 8/2018 |
| DE | 3135983 | | 3/1983 |
| DE | 10044039 | | 3/2002 |
| DE | 20122594 | | 6/2006 |
| EP | 3371508 | | 9/2018 |
| IN | 201817016463 | | 8/2018 |
| TH | 1801002626 | | 3/2019 |
| WO | 2015041672 A1 | | 3/2015 |
| WO | 2017078670 | | 5/2017 |

OTHER PUBLICATIONS

Intellectual Porperty Office of Singapore; Written Opinion, issued in connection with Application No. 11201803617T; dated Aug. 15, 2018; 7 pages; Singapore.

International Search Report and Written Opinion of the Korean Intellectual Property Office dated Jul. 27, 2016 in International Application No. PCT/US2015/058618 filed Nov. 2, 2015.

Patent Office of the Cooperation Council for the Arab States of the Gulf; Examination Report, issued in connection to Application No. GC2015-30311; dated Apr. 29, 2018; 4 pages; GCC.

The International Bureau of WIPO; PCT International Preliminary Report on Patentability, issued in connection to PCT/US2015/058618; dated May 8, 2018; 11 pages; Switzerland.

Australian Government, IP Australia; Examination Report No. 1 for Standard Patent Application, issued in connection to AU2015413844; dated Jan. 16, 2019; 4 pages; Australia.

Canadian Intellectual Property Office; Examiner Report, issued in connection to CA3004049; dated Apr. 15, 2019; 5 pages; Canada.

China National Intellectual Property Administration; First Office Action, issued in connection to CN2015800852926; dated May 29, 2019; 21 pages; China.

Republic of Colombia, Superintendent of Industry and Commercial; Office Action, issued in connection to application No. NC218/0005743; dated May 3, 2019; 9 pagess; Colombia.

European Patent Office; Extended European Search Report, issued in connection to EP15907919.3; dated May 21, 2019; 9 pages; Europe.

Patent Office of the Cooperation Council for the Arab States of the Gulf; Examination Report, issued in connection to Application No. GC2015-30311; dated Jun. 26, 2019; 3 pages; GCC.

Canadian Intellectual Property Office; Examiner Report, issued in connection to CA3004049; dated Jan. 24, 2020; 4 pages; Canada.

Intellectual Property Office of India; First Examination Report, issued in connection to application No. 201817016463; dated Feb. 28, 2020; 8 pages; India.

Indonesian Patent Office; Examination Report, issued in connection to application No. PID201803221; dated Jan. 20, 2020; 4 pages; Indonesia.

Australian Government, IP Australia; Examination Report No. 1 for Standard Patent Application, issued in connection to application No. 2019202648; dated May 4, 2020; 5 pages; Australia.

Intellectual Property Office of Sinapore; Invitation to Respond to Written Opinion, issued in connection application No. 11201803617T; dated Apr. 25, 2020; 7 pages; Singapore.

Republic of Colombia, Superintendent of Industry and Commercial; Office Action, issued in connection to application No. NC2020/0000777; dated Jul. 24, 2020; 4 pages; Colombia.

National Institute of Industrial Property of Ministry of Economy of Brazil; Preliminary Office Action, issued in connection to application No. BR112018008814-5; dated Aug. 25, 2020; 6 pages; Brazil.

Egyptian Patent Office; Official Decision, issued in connection to application No. PCT 742/2018; Sep. 2020; 6 pages; Egypt.

* cited by examiner

REAL TIME INTEGRITY MONITORING OF ON-SHORE PIPES

BACKGROUND

Pipelines used for recovery and transport of fluid or gas generally include many pipe segments joined together in an end-to-end configuration to extend a distance of transport. For example, pipe segments may be joined together to extend up to tens or hundreds or thousands of miles.

Pipelines in the oil and gas industry may be used to transport recovered hydrocarbons, such as crude oil, natural gas, produced water, fracturing fluid, flowback fluid, or other types of gas such as $CO_2$, which may be pumped through the pipeline at a selected flow rate. During transport of crude oil, dissolved waxes found in crude oil can precipitate and build up when subjected to temperatures below or equal to a temperature referred to as the "wax appearance temperature" (WAT) or the "cloud point." The cloud point is specific to each crude composition, and is a function of wax concentration, the concentration of nucleating agents such as asphaltenes and formation fines, and pressure. When enough wax has built up in the pipe, flow of the oil may be restricted, thus reducing efficiency and production. Offshore pipelines are commonly exposed to colder temperatures, and thus, techniques, such as pipe insulation, are implemented to inhibit buildup of wax found in the crude oil. To monitor integrity of the offshore pipelines and clean deposits that have built up within the pipelines, devices know as "pigs" are often sent through the pipelines. For example, some pigs may be used to detect damage to the pipeline, such as dents, corrosion, or cracking.

Onshore pipelines may also be inspected for mechanical damage using pigs. However, as onshore pipelines run above ground and more commonly are buried a few feet below the ground, pipe integrity may also be monitored by walking along the path of the pipe or tubular conduit with various sensing equipment, such as acoustic emission tools, to detect any failure.

SUMMARY OF INVENTION

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a method that includes providing a length of pipeline, the pipeline having a space formed within the thickness of the pipeline housing and extending the length of the pipeline, and continuously monitoring at least one condition within the space to detect in real time if a change in the housing occurs.

In another aspect, embodiments disclosed herein relate to a method that includes providing a length of pipeline, the pipeline having a signal transmitting material disposed within the thickness of the pipeline housing, and continuously receiving a signal from the signal transmitting material to detect a condition of the housing.

In yet another aspect, embodiments disclosed herein relate to a method that includes continuously monitoring temperature along a length of a pipeline, the pipeline having an electrically conducting material disposed within the thickness of the pipeline housing, and applying a current to the electrically conducting material to heat the electrically conducting material when a preselected temperature is detected.

Other aspects and advantages of the invention will be apparent from the following description and the appended claims.

DETAILED DESCRIPTION

Embodiments disclosed herein may relate generally to methods for monitoring pipelines in real time. Pipelines may run onshore and/or through shallow water and extend long distances, such as tens, hundreds or thousands of miles, either aboveground or buried a few feet underground (e.g., ranging from about 3 feet to about 6 feet). Bodies of shallow water may include, for example, rivers, lakes or other bodies of water having depths ranging up to 50 meters, up to 100 meters, or up to 150 meters. In yet other embodiments, pipelines may run offshore, for example through depths of greater than 150 meters, such as greater than 500 meters or greater than 1,000 meters.

Methods according to embodiments of the present disclosure may include providing a length of pipe that may be used for transporting fluids or gas. The pipe may include a housing defining a central bore extending the length of the pipe, through which transported fluids may be pumped. The housing may further have a continuous conduit formed between the thickness of the housing and extending the length of the pipe. As referred to herein, conduits formed or disposed "between" or "within" the thickness of a housing are conduits that are not exposed to the inner or outermost surface of the housing, but rather, are covered or beneath the inner and outermost surfaces of the housing. Further, the pipe may include many pipe segments that are connected together with pipe joints, where the pipe segments and pipe joints are alternatingly connected in an end-to-end configuration.

Figure 1:
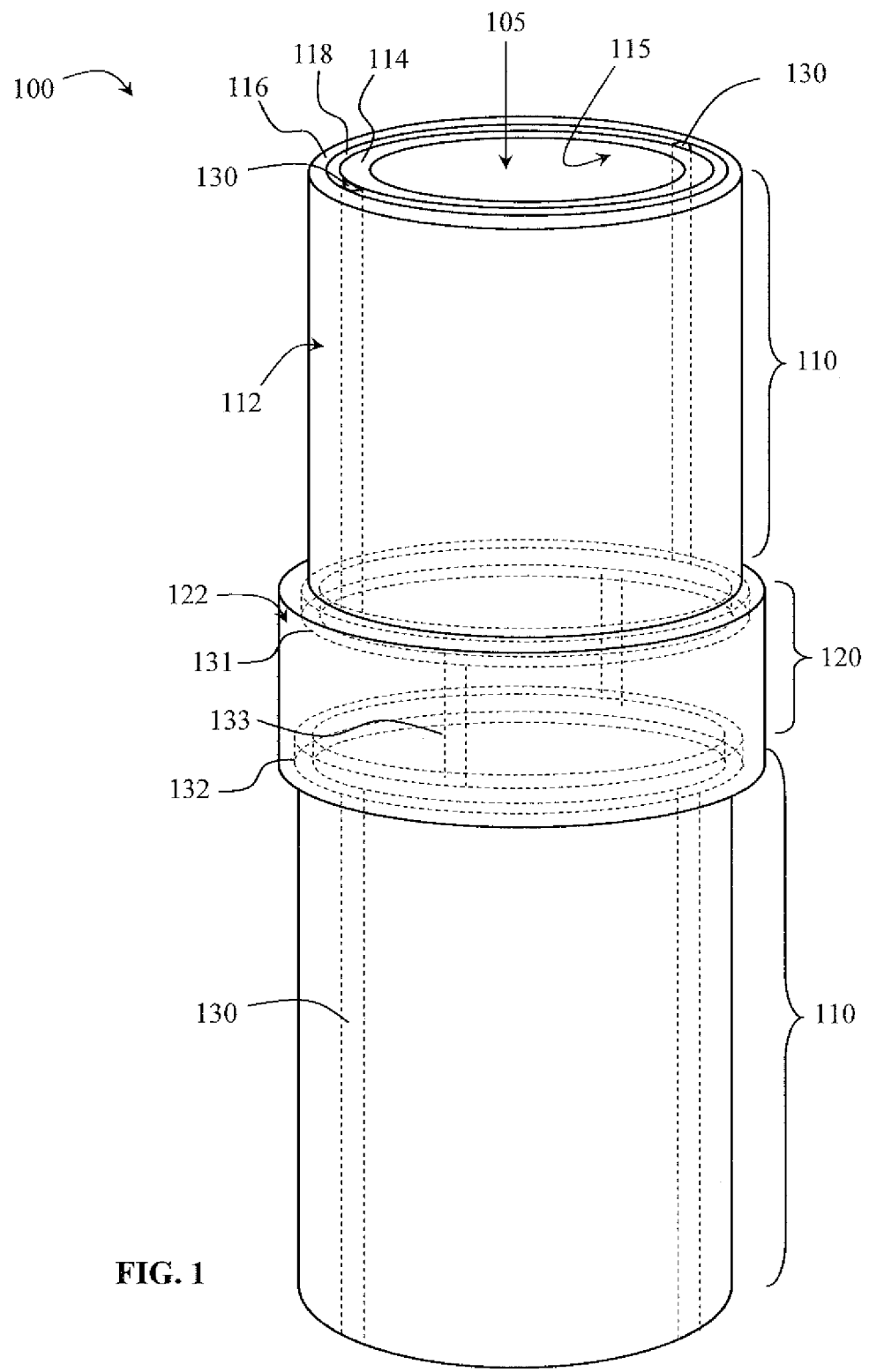
FIG. 1 shows a portion of a pipeline according to embodiments of the present disclosure.

FIG. 1 shows an example of a pipeline according to embodiments of the present disclosure. The pipeline 100 includes pipe segments 110 and pipe joints 120 alternatingly connected together in an end-to-end configuration. The housings of the connected together pipe segments 110 and pipe joints 120 define a central bore 105 extending longitudinally through the length of the pipeline 100, through which fluid and/or gas may flow. The housing 112 of the pipe segments 110 include an inner layer 114 having an inner surface 115 defining the central bore 105. The pipe segment housing 112 further includes an outer shield 116 layer. The outer shield 116 may provide protection from contaminants and damage from environmental elements. The housing thickness is measured between the inner surface 115 and the outermost surface of the housing.

One or more conduits may be formed between the inner layer 114 and the outer shield 116. The conduits formed between the inner layer 114 and outer shield 116 may extend continuously through the length of the pipe segment 110 from one end to the outer end. For example, as shown in FIG. 1, the conduit may be a space 130, which may have, for example, air or other gas flowed there through or held therein. In some embodiments, the conduit may be made of a physical material that is capable of flowing data, light, sound, current, or other signal, for example.

The spaces 130 formed between the inner layer 114 and outer shield 116 may be formed by one or more intermediate layers 118 disposed between the inner layer 114 and outer shield 116. For example, as shown in FIG. 1, the intermediate layer 118 may have two longitudinally extending troughs, which form the spaces 130 when disposed between the inner layer 114 and the outer shield 116. In some embodiments, more than one intermediate layer may be disposed between an inner layer and an outer shield, where the intermediate layers may individually or together form one or more spaces. For example, two or more intermediate layers partially corresponding in shape may be concentrically disposed between an inner layer and outer shield, where portions of non-corresponding shape may form spaces between the intermediate layers. Further, in some embodiments, intermediate layers may be provided by one or more layers of wound strip helically disposed between the inner layer and outer shield of a housing, where spaces may be formed between the wound strips.

Intermediate layers may have a substantially flat cross section, or may have predetermined cross sectional shapes that are not flat, e.g., rounded, rough, raised, or other non-planar shapes. In embodiments having intermediate layers with a cross sectional shape that is not flat, non-planar portions of the intermediate layers may be used to form spaces extending the length of the pipe segment. Intermediate layers, including intermediate layers formed of one or more strips, may or may not interlock to some extent.

Pipe segments may be joined in an end-to-end configuration using pipe joint, where conduits formed through the pipe segment housing may be fluidly connected via conduits formed through the pipe joint. For example, as shown in FIG. 1, the pipe joint 120 may have a pipe joint housing 122 having a first annular space 131 at a first end of the pipe joint and a second annular space 132 at a second end of the pipe joint, and one or more spaces 133 longitudinally extending from the first annular space 131 to the second annular space 132. Each of the pipe segments 110 may be connected to the ends of the pipe joint 120 such that the openings of spaces 130 in each pipe segment 110 open to the annular spaces 131, 132, thereby contiguously communicating the spaces 130 in each pipe segment 110. In some embodiments, a pipe joint may have spaces extending longitudinally through the pipe joint housing, where the openings of the pipe joint spaces may align with openings of adjacent pipe segment spaces, thereby forming a contiguous and continuously extending space through the entire length of the pipeline. Other means of fluidly communicating pipe segment spaces through one or more spaces formed in a pipe joint housing may be used to provide a continuous spatial conduit through the entire length of the pipeline.

Further, although pipe segment spaces 130 and pipe joint spaces 133 are shown as extending linearly along the length of the housings 112, 122, other continuously extending spatial paths may be formed through the housings of the pipe segments and pipe joints. For example, in some embodiments, strips of material forming a first intermediate layer may be helically wrapped around an inner layer such that relatively small gaps or spaces (e.g., 5-10% of the width of the strip) are formed between adjacent strips. One or more additional intermediate layers may be disposed around the first intermediate layer (overlapping the first intermediate layer), such that the gaps formed between adjacent strips may be partially enclosed to form one or more spaces opening at both ends of the pipe segment. In such embodiments, the formed spaces may extend along the length of the housing in a helical path. In some embodiments, different shapes of spaces may be contiguous to each other, forming an irregular-shaped but continuous conduit through the entire length of a pipeline.

Pipe segments may be connected together via pipe joints in an end-to-end configuration, for example, by interlocking end shapes (between an end of a pipe joint and an end of a pipe segment), interference fitting, bolting, gluing, welding, by fastening jackets or sleeves around abutting ends, as well as other fastening techniques.

FIG. 1 shows a pipeline 100 having two pipe segments joined together in an end-to-end configuration via pipe joint 120. However, it will be understood that a pipeline may be formed by two or more pipe segments each joined to one or two adjacent portions of pipe by a respective connection. The pipe segments may be rigid or flexible.

According to embodiments of the present disclosure, one or more layers of a pipe segment may be formed of a flexible material. For example, as shown in FIG. 1, the inner layer 114 and outer shield 116 may be formed of a flexible material that is extruded into a tubular shape. Pipe segments having one or more layers formed of a flexible material may be referred to as flexible pipes. Flexible pipes may have an inner layer defining a central bore or flow through that is extruded from a flexible material. One or more intermediate layers (e.g., strips, tapes, wrapped layers) may be applied around the inner extruded layer such that at least one conduit extends the length of the pipe. An outer layer of a flexible material may then be extruded over the intermediate layers to form an outer shield. In some embodiments, more than one flexible material may be extruded around the inner layer and/or outer shield. Flexible material may include, for example, polymers and fiber embedded polymers, such as steel, aluminum, beryllium, or copper alloy fibers embedded within a polymer. Suitable polymers may include, for example, olefin polymers blended with at least one thermoset elastomer, or polyolefins.

Intermediate layers may be formed of, for example, steel, carbon steel, or other metal composite layers, a plurality of relatively narrow strips of material disposed in a side-by-side relation; a high strength tape with oriented polymer chains; tapes reinforced with fibers, composites of strength-adding polymers, or strips of other metals; polymers, such as polyethylene or polypropylene, reinforced with metallic fibers; or other tapes containing metal reinforcements, including steel, aluminum, or copper alloys. Intermediate layers may be formed of a stronger material than the material forming an inner layer, for example, to provide pressure reinforcement to prevent bursting of the inner layer and to prevent collapse of the pipe from external pressures.

According to embodiments of the present disclosure, methods of monitoring a pipeline may include monitoring a conduit formed within the housing of the pipeline and extending the length of the pipeline. For example, a length of pipeline may be provided, the pipeline having a housing defining a central bore extending the length of the pipeline, and a space formed within the housing and extending the length of the pipeline. The pipeline may be formed of a plurality of pipe segments connected together by pipe joints in an end-to-end configuration, where the pipe segment housings and pipe joint housings together form the housing of the pipeline having the space continuously extending there through.

At least one condition within the space of the pipeline housing may be continuously monitored to detect in real time if a change in the housing occurs. For example, in some embodiments, the pressure within a space extending through a pipeline housing may be continuously monitored. The space may include a plurality of pressure transducers disposed within the space along the length of the space. Pressure transducers may include, for example, thin-film type pressure transducers, piezoelectric pressure transducers, or any other pressure sensing element capable of generating a signal as a function pressure sensed. The pressure transducers may continuously monitor the pressure within the space and send signals to a user, storage device, alert system, or other end component relaying the pressure detected. Changes in pressure within the space may indicate in real time, for example, a breach in the housing or a change in the environment surrounding the pipeline housing which may damage the housing.

In some embodiments, a space extending the length of the pipeline may be precharged to have a preset pressure. For example, the space may be filled with a predetermined amount of inert gas, such as nitrogen. Pressure transducers may be disposed within the space to monitor the pressure within the space. Detection of a drop in pressure may indicate in real time that damage to the housing has occurred.

Figure 2:
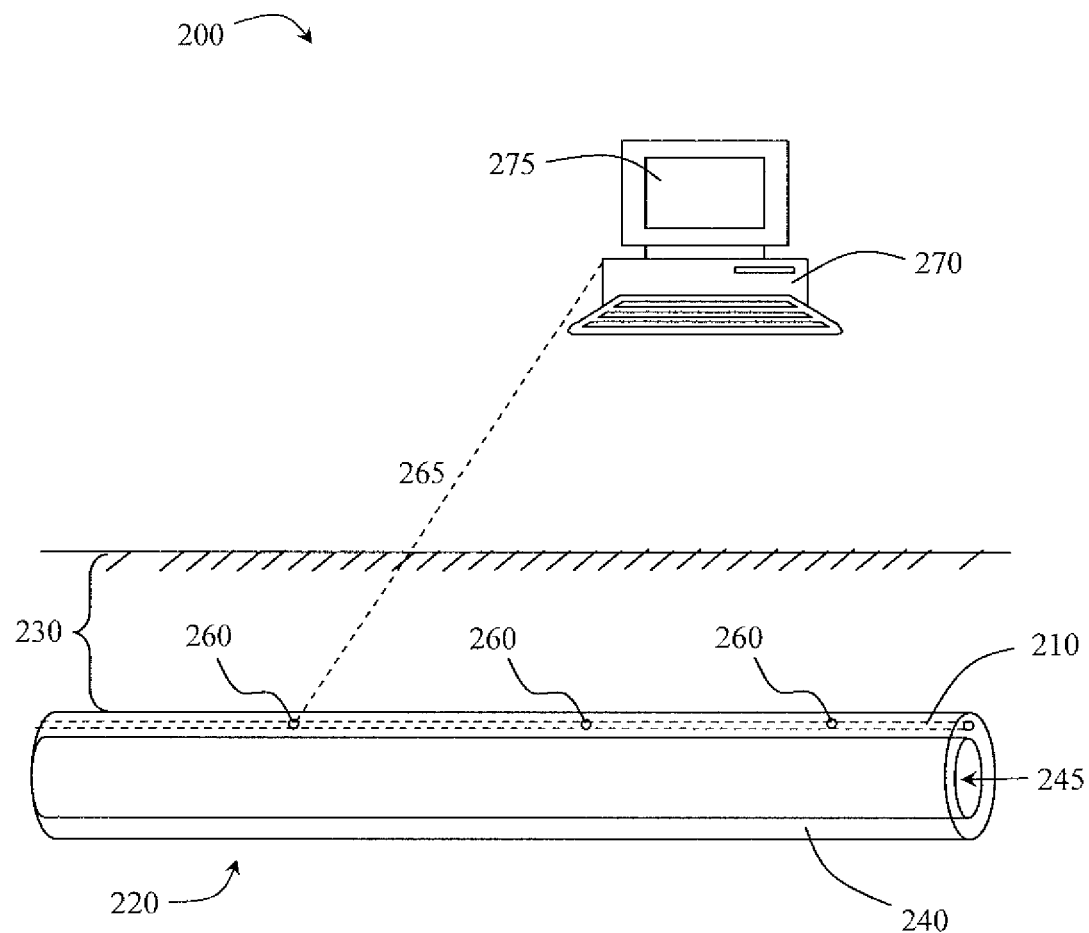
FIG. 2 shows a diagram of a system according to embodiments of the present disclosure.

FIG. 2 shows an example of a system 200 for continuously monitoring pressure within a space 210 extending the entire length of a pipeline 220. The pipeline 220 may be an onshore pipeline, which may extend a distance across land (e.g., in a direction substantially parallel with the surface of the land), partially or completely buried a shallow depth 230 underground, and/or may extend through shallow water. For example, in some embodiments, a majority (e.g., greater than 50%, greater than 75% or greater than 90%) of the length of a pipeline may be buried underground a depth ranging from, for example, less than 10 ft, less than 7 ft, or less than 5 ft. The pipeline 220 may have a housing 240 defining a central bore 245, through which fluid or gas may flow or be stored, where at least one enclosed space 210 may be formed within the thickness of the housing 240 and fluidly or continuously extend the entire length of the pipeline 220. At least one pressure transducer 260 may be disposed within the space 210 or along the length of the pipeline 220. The pressure transducer(s) 260 may detect the pressure within the space 210 and generate a signal indicating the pressure. The pressure signal 265 may be sent wirelessly or through an additional conduit disposed within the thickness of the pipeline housing that is capable of transmitting data or signals (discussed more below). The pressure signal may be transmitted to a receiver. The receiver may be part of a computing device 270 or may be a storage device accessible to a computing device.

For example, a computing device 270 may include a computer processor and memory having instructions (e.g., one or more software programs) executing on the computer processor with functionality to receive pressure signals transmitted from the pressure transducers. The computing device may process received signals continuously and may display results on a graphical user interface 275, such as a screen, in various formats, such as a graph, chart, etc. Further, in some embodiments, a computing device 270 may have an alert program, which may generate an alert when a preselected pressure condition is detected. For example, if a change in pressure over a predetermined amount is detected (e.g., a 5% change, a 10% change, a 15% change), an alert may be generated.

In some embodiments, a gas having a predetermined composition may be disposed within a space formed through a pipeline housing, where the gas composition may be continuously monitored. In some embodiments, the gas composition may be continuously monitored by continuously flowing a gas having the predetermined composition through the space. The gas may be flowed through the space, for example, by pumping the gas into the space and venting the gas through at least one venting port formed in the housing. Gas composition may be tested after the gas exits at least one venting port formed in the housing. In some embodiments, gas composition may be continuously monitored by extracting a gas from at least one venting port formed in the pipeline housing at an interval and testing the gas composition of the gas after extraction. For example, gas may be extracted from a space formed within a pipeline housing twice a day, once a day, twice a week, once a week, or other selected interval, and tested to determine if the tested composition has changed from the predetermined composition. A change in gas composition may indicate, for example, that corrosion or a breach in the pipeline housing has occurred.

The temperature within a space formed through the entire length of a pipeline may be continuously monitored, alone or in combination with monitoring other conditions of the space. For example, temperature and pressure may be continuously monitored through one or more conduits formed between the thickness of a pipeline housing, where temperature measurements may be compared with the pressure measurements, for example, to determine if a measured pressure change is from a change in temperature from the external environment. Temperature within a conduit (e.g., a space) formed through a pipeline housing may be continuously monitored with one or more temperature sensors. Suitable temperature sensors may include, for example, thermistors, thermocouples, or other sensors capable of producing an electrical signal in response to a change in temperature. Signals indicating temperature measurements may be transmitted, for example, wirelessly or through a conduit disposed within the thickness of the pipeline housing that is capable of transmitting signals.

According to embodiments of the present disclosure, methods of monitoring a pipeline, in real time, may include providing a length of pipeline that has a housing defining a central bore extending the length of the pipeline and at least one conduit formed within the thickness of the housing and extending the entire length of the pipeline. The conduit may be a signal transmitting material or other physical material that is capable of flowing data, light, sound or current disposed between at least two layers forming the inner surface and outer surface of the pipeline housing. For example, a conduit of signal transmitting material may be disposed between an inner layer and an outer shield of a flexible pipe. One or more conditions within the thickness of the pipeline housing may be measured and continuously monitored. For example, a signal transmitting material forming one or more conduits through the thickness of a pipeline housing may continuously detect a condition of the housing and generate signals representing the condition. The signals may be transmitted through the signal transmitting material to monitor in real time the condition of the housing.

According to embodiments of the present disclosure, a conduit formed of a signal transmitting material (disposed between the thickness of the housing and extending the entire length of the pipeline) may include an electrically conducting material. The electrically conducting material may be used to transmit signals from one or more sensors, such as disclosed herein. In some embodiments, the electrically conducting material may be both a sensor and a transmitter, where an electrical current may be applied through the electrically conducting material and changes in one or more conditions of the pipeline housing may be detected by a voltage drop through the electrically conducting material. For example, a breach in the housing or corrosion in the housing may alter the environment in which the electrically conducting material is disposed, which may alter the flow of the current being applied thereto. In some embodiments, a signal transmitted by an electrically conducting material may include a voltage drop occurring across the electrically conducting material from a change in the housing, such as a breach or dent in the housing. The resistivity through the electrically conducting material may be used to back-calculate a location of the change resulting in the measured voltage drop.

Electrically conducting material may be provided in the form of strips that are applied in at least one intermediate layer (disposed between an inner surface defining the pipe's central bore and the outer surface of the pipe). One or more strips of electrically conducting material may be provided, for example, linearly along the length of the pipe or at an angle with respect to the pipe's length such that the strip(s) extend helically along the length of the pipe. Strips of electrically conducting material may have a width ranging, for example, less than 50% of the outer circumference of the pipe, less than 20% of the outer circumference of the pipe, less than 10% of the outer circumference of the pipe, or less than 5% of the outer circumference of the pipe. In some embodiments, electrically conducting material may be in the form of one or more wires. Wires may have a diameter ranging, for example, less than 15% of the housing thickness (measured from the pipe's inner surface to the outer surface), less than 10% of the housing thickness, or less than 5% of the housing thickness.

For example, electrically conducting material may be provided in the form of at least two wires as a signal transmitting conduit through a pipeline housing. A voltage may be applied to a first wire of the at least two wires, and the voltage along a second wire (spaced apart from the first wire) may be measured to detect resistivity between the first and second wires. Such a configuration of wire pairs disposed between the thickness of the pipeline housing may be used, for example, to detect moisture within the pipeline housing, where an increase in moisture may indicate a breach in the housing. In such embodiments, moisture collected between the spaced apart wires may provide a path for current to flow (lower the resistivity between the spaced apart wires), and when voltage is applied to the first wire, the measured voltage from the second spaced apart wire may indicate the resistivity between the two wires. Two spaced apart wires may be provided within a pipeline housing (as a conduit disposed between an inner layer and an outer of the pipe housing) or more than two spaced apart wires may be provided. In some embodiments, multiple pairs of wires may be provided in a mesh configuration (e.g., as a Faraday mesh) to detect moisture across a large areas (e.g., up to the entire circumference and extending up to the entire length) within the thickness of the pipeline housing.

In some embodiments, signal transmitting material may be provided in the form of a mesh outside of the thickness of the pipe housing, for example, around the outer shield of a pipe. An insulating tape or layer of insulating material may then be applied over the outer mesh to insulate the outer mesh line of communication.

Embodiments having an electrically conducting material extend along the length of pipe segments and within the thickness of the pipe housing may include pipe joints capable of connecting the pipe segments together and transmitting signals carried through the electrically conducting material between adjacent pipe segments. A pipe joint may be configured to connect electrically conducting material extending through adjacent pipe segments by having an electrically conducting material extend between two openings formed at opposite axial ends of the pipe joint, where axial ends of the adjacent pipe segments are inserted into the openings of the pipe joint and electrically conducting material exposed at the axial ends of the pipe segments are contacted to electrically conducting material in the pipe joint. Electrically conducting material in the pipe segments and pipe joints may be insulated from the outer environment in which the pipeline is installed.

Figure 3:
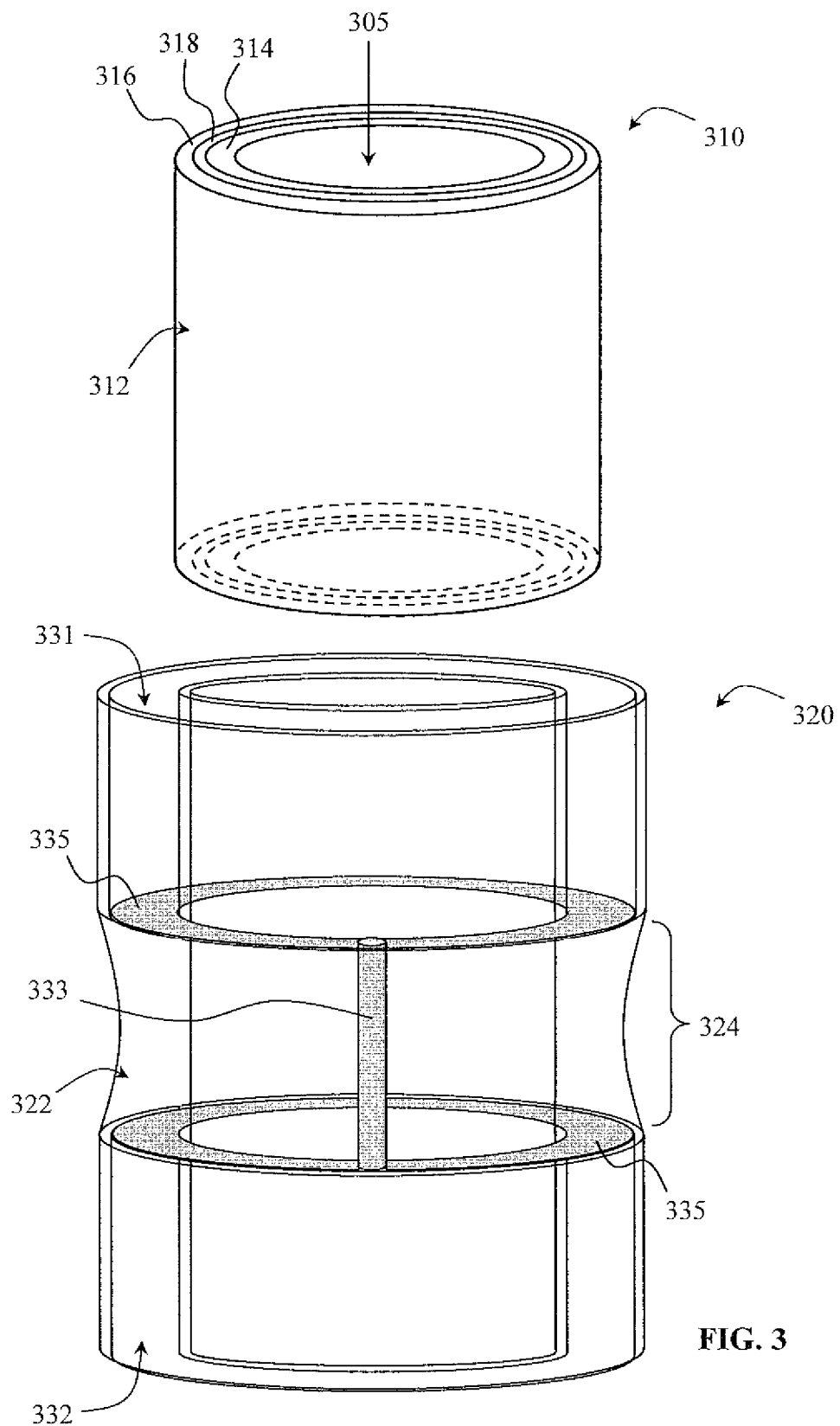
FIG. 3 shows a diagram of a pipe segment and pipe joint according to embodiments of the present disclosure.

FIG. 3 shows an example of a pipe joint and pipe segment having electrically conducting material therein configured to connect together. The lengths of the pipe segment 310 and pipe joint 320 are not shown to scale. Further, the pipe joint 320 is shown as being partially transparent to show interior portions and elements disposed therein.

The pipe segment 310 has a housing 312 defining a central bore 305, where the housing 312 includes an inner layer 314, an outer layer 316, and at least one intermediate layer 318 disposed between the inner and outer layers 314, 316. The intermediate layer 318 may include at least one layer, strip or wire made of electrically conducting material extending the length of the pipe segment and exposed at each axial end of the pipe segment 310. Electrically conducting material disposed between the thickness of the pipe segment 310 may be insulated from the environment in which the pipeline is disposed, for example, by forming the outer and inner layers 314, 316 with electrically insulating material or by providing an electrically insulating material around all surfaces of the electrically conducting material except the portions exposed at the axial ends for connection to other electrically conducting material. For example, an insulating material may be coated or layered around electrically conducting layer(s), strip(s) or wire(s), where all portions of the electrically conducting layer(s), strip(s) or wire(s) except those exposed at the axial ends of pipe segment are covered by the electrically insulating material. By exposing the electrically conducting material to the axial end of the pipe segment 310, the electrically conducting material may be contacted to an electrically conducting material disposed through pipe joint 320.

As shown, pipe joint 320 includes a pipe joint housing 322 having a first annular space 331 at a first axial end of the pipe joint and a second annular space 332 at a second axial end of the pipe joint, where axial ends of pipe segments may be inserted into the first and second annular spaces 331, 332 of the pipe joint to connect the pipe segments together. An axial end of pipe segment 310 may be inserted into the first or second annular space 331, 332 and secured therein, for example, by interference fitting between the axial end of the pipe segment 310 and the annular space within the pipe joint 320. In some embodiments, an axial end of the pipe segment 310 may be inserted into a first or second annular space 331, 332 formed in the pipe joint 320, and the outer surface around the annular space may be compressed radially inward to secure the inserted axial end of the pipe segment. An interior portion 324 of the pipe joint 320 (disposed between the first and second annular spaces 331, 332) may have a thickness less than (as shown), greater than, or equal to the thickness measured between the inner surface and outer surface along the first and second annular spaces 331, 332.

An electrically conducting material 333 (e.g., in the form of a layer, strip or wire) may be disposed within the thickness of the pipe joint 320, between the outermost surface of the pipe joint and the inner surface of the pipe joint defining a central bore 305 extending there through. The pipe joint electrically conducting material 333 may be electrically insulated from the environment in which the pipe joint is disposed, for example, by forming the outermost surface and inner surface with electrically insulating material or by coating the electrically conducting material 333 with electrically insulating material, such that end portions of the electrically conducting material 333 remain uncoated for electrical communication with the electrically conducting material in the adjacent pipe segments. In some embodiments, an electrically conducting ring 335 may be disposed at the base of each annular space 331, 332, where the electrically conducting material 333 extends from a first electrically conducting ring 335 in the first annular space 331 to a second electrically conducting ring 335 in the second annular space 332. The electrically conducting material 33 may contact and transfer electrical signals between the first and second conducting rings 335, while also being electrically insulated between the pipe joint thickness. When axial ends of pipe segments are inserted into the annular spaces 331, 332, the electrically conducting material exposed at the axial ends of the pipe segments may contact and transfer electrical signals to the electrically conducting ring 335. In such a manner, connected together pipe segments and pipe joints having electrically conducting material extending there through may have electrical signals transferred through a first electrically conducting material in a first pipe segment connected to a pipe joint, through a first electrically conducting ring in the pipe joint, through pipe joint electrically conducting material, through a second electrically conducting ring in the pipe joint, through a second electrically conducting material in a second pipe segment connected to the pipe joint, and so forth, until the signal is transferred the length of the pipeline.

By providing the electrically conducting rings, between electrically conducting material extending through adjacent pipe segments and pipe joints, pipe joint electrically conducting material does not need to be aligned with pipe segment electrically conducting material. However, according to some embodiments of the present disclosure, electrically conducting material in pipe segments may be aligned with electrically conducting material in a pipe joint (without the use of an electrically conducting ring). Further, in some embodiments, electrically conducting material may be provided in shapes other than rings to electrically conduct pipe joint electrically conducting material with pipe segment electrically conducting material. For example, one or more clips (e.g., T-shaped clips) may extend between the connection of a pipe segment to a pipe joint to electrically connect the pipe joint electrically conducting material with the pipe segment electrically conducting material. In some embodiments, a clip or other connecting component formed of electrically conducting material may be inserted into an axial end of a pipe segment and contact electrically conducting material disposed within the pipe segment, where an exposed portion of the connecting component may contact pipe joint electrically conducting material when the axial end of the pipe segment secured to the pipe joint.

Further, in some embodiments, a pipe joint may be partially or entirely formed of electrically conducting material, where electrically conducting material exposed at an axial end of a pipe segment may contact the pipe joint electrically conducting material upon securing the pipe segment to the pipe joint. An electrically insulating material may be disposed around the pipe joint, e.g., by wrapping the pipe joint with an electrically insulating tape or spray coating with an electrically insulating material, to electrically insulate the signals being transmitted through the electrically conducting material.

Other configurations of connecting electrically conducting material through pipe segments and pipe joints may be used, where electrically conducting material extending through the lengths of the pipe segments and through connecting portions in pipe joints may be electrically insulated from the environment in which the pipe is disposed. For example, the outer surface and/or the inner surface of pipeline housing may having electrically insulating material applied thereto, for example, with electrically insulating tape or by spray coating the electrically insulating material thereto.

According to embodiments of the present disclosure, methods of monitoring a pipeline may include altering at least one condition of the pipeline in response to the monitoring. For example, in some embodiments, temperature along a length of a pipe may be continuously monitored, where the pipeline has a housing defining a central bore extending the length of the pipeline, and the housing has an electrically conducting material disposed between two layers: an inner layer forming an inner surface of the housing and an outer layer forming an outer surface of the housing. A preselected temperature or temperature range may be selected, for example, depending on the environment in which the pipeline is disposed and/or the fluid or gas being disposed within the pipeline. In some embodiments, the preselected temperature may be a minimum temperature for maintaining one or more conditions of the fluid or gas being disposed within the pipeline. When the preselected temperature is detected, a current may be applied to the electrically conducting material to heat the electrically conducting material.

For example, in some embodiments monitoring a pipeline carrying crude oil, a preselected temperature may be a wax appearance temperature, or "cloud point," of the crude oil. The temperature may be continuously monitored through one or more electrically conducting conduits disposed within the thickness of the pipeline housing and extending the entire length of the pipeline. When a temperature less than or equal to the cloud point is detected, a current may be applied to the electrically conducting material and shorted to heat the region in which the preselected temperature was detected. By heating the region of the pipeline in which temperatures less than or equal to the cloud point are detected, wax nucleation and build up may be prevented or inhibited in the crude oil. Such embodiments may be used when a pipeline carrying crude oil extends through a colder environment, such as across land in northern regions of North America, Asia or Europe or in southern regions of South America.

The temperature of an electrically conducting material disposed within the thickness of a housing may be continuously monitored, for example, temperature sensors, or other sensing types disclosed herein.

By providing a pipeline having a continuous conduit pathway through the entire length of the pipeline, and monitoring the conduit, one or more conditions of the pipeline housing may be continuously monitored, and changes in the one or more conditions may be detected in real time. For example, rather than periodically sending a sensing device along a pipeline to measure one or more conditions of the pipeline, the conduit extending through pipelines of the present disclosure may be continuously monitored without affecting operations of the pipeline.

Further, rather detecting one or more problems with a pipeline (such as by observing changes in flow through the pipeline's central bore) and then sending one or more device along the pipeline to detect where the problem originates, methods disclosed herein may allow for detection of a problem initiation, in real time, and, in some embodiments, indication of where the problem initiation occurs. For example, continuous monitoring methods disclosed herein may allow for the early stage detection of corrosion initiation, dents or cracks in the housing, or other problem initiations (e.g., through early stage detection of a change in gas composition, changes in current flow through the conduit, or other monitoring techniques disclosed herein) before complete failure in the pipeline housing occurs (e.g., a breach in the housing resulting in leakage), thereby providing the opportunity to repair or replace sections of the pipeline before the section of the pipeline fails.

Although only a few example embodiments have been described in detail above, those skilled in the art will readily appreciate that many modifications are possible in the example embodiments without materially departing from the scope of this disclosure. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112(f) for any limitations of any of the claims herein, except for those in which the claim expressly uses the words "means for" together with an associated function.

What is claimed is:

1. A method, comprising:
providing a length of pipeline, the pipeline comprising:
a housing defining a central bore extending the length of the pipe;
a space formed within the housing and extending the length of the pipe;
a plurality of pipe segments; and
at least one pipe joint connecting adjacent pipe segments together in an end-to-end configuration, wherein the space continuously extends through the pipe segments and the at least one pipe joint; and
continuously monitoring at least one condition within the space to detect in real time if a change in the housing occurs.

2. The method of claim 1, wherein the space comprises a predetermined amount of gas, and the at least one condition being continuously monitored comprises pressure.

3. The method of claim 2, wherein at least one pressure transducer continuously monitors the pressure of the space.

4. The method of claim 2, further comprising monitoring temperature along the pipe and comparing the pressure to the temperature to determine if a pressure change is from a temperature change.

5. The method of claim 1, wherein a gas composition within the space is continuously monitored.

6. The method of claim 5, wherein the gas composition is continuously monitored by continuously flowing a gas through the space and testing the gas after the gas exits at least one venting port formed in the housing.

7. The method of claim 5, wherein the gas composition is continuously monitored by extracting a gas from at least one venting port formed in the housing at an interval and testing the gas composition of the gas after extraction.

8. A method, comprising:
providing a length of pipeline, the pipeline comprising:
a housing defining a central bore extending the length of the pipeline, the housing comprising:
a thickness measured between an inner surface of the housing and an outer surface of the housing; and
a signal transmitting material disposed between the thickness of the housing;
a plurality of pipe segments; and
at least one pipe joint connecting adjacent pipe segments together in an end-to-end configuration, wherein the signal transmitting material continuously extends through the pipe segments and the at least one pipe joint; and
continuously receiving at a receiver a signal from the signal transmitting material to detect a condition of the housing.

9. The method of claim 8, wherein the signal transmitting material comprises an electrically conducting material.

10. The method of claim 9, wherein the electrically conducting material is electrically insulated within the thickness.

11. The method of claim 9, further comprising applying an electrical current through the signal transmitting material, wherein the condition being detected is a voltage drop across the signal transmitting material.

12. The method of claim 9, wherein the signal transmitting material comprises at least two wires, and further comprising:
applying a voltage to a first wire of the at least two wires; and
measuring voltage along a second wire of the at least two wires, the signal comprising the measured voltage;
wherein the condition detected by the measured voltage is moisture.

13. The method of claim 9, wherein the signal transmitting material forms a Faraday cage around the longitudinal conduit.

14. The method of claim 9, wherein the signal comprises a voltage drop from a change in the condition of the housing, further comprising determining an amount of resistivity through the voltage drop to calculate a location of the change.

15. The method of claim 8, wherein each of the at least one pipe joint comprises:
an annular space formed at each axial end of the pipe joint;
an electrically conducting ring disposed at a base of each annular space; and
an electrically conducting material contacting each electrically conducting ring; and
wherein the signal transmitting material in the pipe segments contact the electrically conducting rings in each pipe joint.

16. The method of claim 8, further comprising disposing an electrically insulating material at least around the at least one pipe joint in the length of pipe, wherein the signal transmitting material is an electrically conducting material, and wherein the at least one pipe joint is formed of the electrically conducting material.

17. A method, comprising:
    continuously monitoring temperature along a length of a pipeline, the pipeline comprising a housing having an inner surface defining a central bore extending the length of the pipe, an outer surface, and an electrically conducting material disposed between the inner surface and the outer surface; and
    applying a current to the electrically conducting material to heat the electrically conducting material when a preselected temperature is detected.

18. The method of claim 17, wherein temperature is continuously monitored with at least one temperature sensor, and wherein signals from the at least one temperature sensor are transmitted through the electrically conducting material.

19. The method of claim 1, wherein each of the at least one pipe joint comprises:
    a first annular space at a first end of the pipe joint;
    a second annular space at a second end of the pipe joint; and
    one or more spaces longitudinally extending from the first annular space to the second annular space.

20. The method of claim 8, wherein each of the at least one pipe joint comprises:
    a first annular space at a first end of the pipe joint;
    a second annular space at a second end of the pipe joint; and
    one or more spaces longitudinally extending from the first annular space to the second annular space.

* * * * *

UNITED STATES PATENT AND TRADEMARK OFFICE
CERTIFICATE OF CORRECTION

PATENT NO. : 10,948,130 B2
APPLICATION NO. : 15/773109
DATED : March 16, 2021
INVENTOR(S) : Ethridge et al.

It is certified that error appears in the above-identified patent and that said Letters Patent is hereby corrected as shown below:

In the Specification

Column 1, Line 30, delete "know" and insert --known--.

Column 5, Line 11, delete "function pressure sensed" and insert --function of pressure sensed--.

Column 7, Line 59, delete "across a large areas" and insert --across large areas--.

Column 8, Line 35, delete "outer and inner" and insert --inner and outer--.

Column 9, Line 24, delete "33" and insert --333--; Column 9, Line 65, delete "segment secured" and insert --segment is secured--.

Column 10, Line 61, delete "example, temperature" and insert --example, using temperature--.

Column 11, Line 6, delete "rather detecting" and insert --rather than detecting--; Column 11, Line 8, delete "device" and insert --devices--.

In the Claims

Column 11, Line 44, Claim 1, delete "pipeline, the pipeline" and insert --pipe, the pipe--.

Column 12, Line 10, Claim 8, delete "pipeline, the pipeline" and insert --pipe, the pipe--; Column 12, Line 12, Claim 8, delete "pipeline" and insert --pipe--; Column 12, Line 46, Claim 13, delete "the longitudinal" and insert --a longitudinal--.

Column 13, Line 5, Claim 17, delete "pipeline, the pipeline" and insert --pipe, the pipe--.

Signed and Sealed this
Twentieth Day of December, 2022

Katherine Kelly Vidal
*Director of the United States Patent and Trademark Office*